US008643648B2

(12) United States Patent
Heywood et al.

(10) Patent No.: US 8,643,648 B2
(45) Date of Patent: Feb. 4, 2014

(54) SYSTEMS, METHODS, AND COMPUTER-READABLE MEDIA FOR CONTEXT-LINKED IMPORTATION OF USER INFORMATION

(75) Inventors: James Heywood, Newton, MA (US); Paul Wicks, Boston, MA (US)

(73) Assignee: PatientsLikeMe, Inc., Cambridge, MA (US)

( * ) Notice: Subject to any disclaimer, the term of this patent is extended or adjusted under 35 U.S.C. 154(b) by 282 days.

(21) Appl. No.: 12/751,270

(22) Filed: Mar. 31, 2010

(65) Prior Publication Data

US 2010/0245358 A1 Sep. 30, 2010

Related U.S. Application Data

(63) Continuation of application No. PCT/US2010/029208, filed on Mar. 30, 2010.

(60) Provisional application No. 61/165,463, filed on Mar. 31, 2009.

(51) Int. Cl.
*G06T 11/60* (2006.01)
(52) U.S. Cl.
USPC .......................................................... 345/440
(58) Field of Classification Search
USPC .......................................................... 345/440
See application file for complete search history.

(56) References Cited

U.S. PATENT DOCUMENTS

| 5,830,149 | A  | * | 11/1998 | Oka et al. ...................... 600/500 |
| 6,567,411 | B2 | * | 5/2003  | Dahlen ........................... 370/401 |
| 7,203,704 | B1 |   | 4/2007  | Stern et al. |
| 7,761,311 | B2 | * | 7/2010  | Clements et al. ................. 705/3 |
| 7,809,376 | B2 | * | 10/2010 | Letourneau et al. .......... 455/445 |
| 2003/0023461 | A1 | * | 1/2003 | Quintanilla et al. .............. 705/3 |
| 2004/0078237 | A1 | * | 4/2004 | Kaafarani et al. ................. 705/2 |
| 2006/0104515 | A1 |   | 5/2006 | King et al. |
| 2007/0123223 | A1 | * | 5/2007 | Letourneau et al. ....... 455/414.1 |
| 2007/0239761 | A1 |   | 10/2007 | Baio et al. |
| 2008/0010089 | A1 | * | 1/2008 | DiMaggio et al. ................ 705/2 |
| 2008/0071580 | A1 |   | 3/2008 | Marcus et al. |
| 2009/0125333 | A1 |   | 5/2009 | Heywood et al. |
| 2009/0131758 | A1 |   | 5/2009 | Heywood et al. |
| 2009/0144089 | A1 |   | 6/2009 | Heywood et al. |
| 2010/0145774 | A1 | * | 6/2010 | Veshnyakov et al. .......... 705/12 |
| 2010/0180213 | A1 | * | 7/2010 | Karageorgos et al. ........ 715/753 |

OTHER PUBLICATIONS

R. Baeza-Yates & B. Ribiero-Neto, "Modern Information Retrieval" § 7.2 (1999).

(Continued)

*Primary Examiner* — Javid A Amini
(74) *Attorney, Agent, or Firm* — Edwards Wildman Palmer LLP; Ralph A. Loren; Jonathon P. Western

(57) ABSTRACT

Various aspects of the invention described herein provide systems and methods for context-linked importation of user information. One aspect of the invention provides a method for context-linked importation of user information. The method includes: providing an interactive environment that allows posting of content by a plurality of pre-identified users; receiving content for the interactive environment from a pre-identified user; selecting relevant data about the pre-identified user from a database, the relevant data selected based on information contained in the content; and displaying the relevant data along with the content on the interactive environment.

19 Claims, 10 Drawing Sheets

(56) References Cited

OTHER PUBLICATIONS

Catherine A. Brownstein et al., "The power of social networking in medicine," 27(10) Nature Biotechnology 888-90 (Oct. 2009).

Jeana H. Frost & Michael P. Massagli, "Social Uses of Personal Health Information Within PatientsLikeMe, an Online Patient Community: What Can Happen When Patients Have Access to One Another's Data," 10(3) J. Med. Internet Res. e15 (May 27, 2008).

Jeana Frost & Michael Massagli, "Social Uses of Personal Health Information Within PatientsLikeMe," (Sep. 4, 2008).

Thomas Goetz, "Practicing Patients," N.Y. Times Magazine (Mar. 25, 2008).

International Search Report for International Application No. PCT/US10/29208 (May 17, 2010).

G. Minnen et al., "Applied morphological processing of English," 7(3) Natural Language Engineering 207-23 (2001).

Paul Wicks & Graeme J.A. MacPhee, "Pathological Gambling Amongst Parkinson's Disease & ALS Patients in an Online Community (PatientsLikeMe.com)," 24(7) Movement Disorders 1085-88 (2009).

P. Wicks et al., "Measuring function in advanced ALS: validation of ALSFRS-EX extension items," 16 European J. Neurology 353-359 (2009).

Written Opinion of the International Searching Authority for International Application No. PCT/US10/29208 (May 17, 2010).

P. Wicks & J. Frost, "ALS patients request more information about cognitive symptoms," 15(5) Europe J. Neurology 497-500 (Mar. 6, 2008).

\* cited by examiner

SYSTEMS, METHODS, AND COMPUTER-READABLE MEDIA FOR CONTEXT-LINKED IMPORTATION OF USER INFORMATION

RELATED APPLICATIONS

This application is a continuation of International Application No. PCT/US10/29208, filed on Mar. 30, 2010. This application also claims priority to U.S. Provisional Patent Application Ser. No. 61/165,463, filed on Mar. 31, 2009. This entire contents of these applications are hereby incorporated by reference herein.

TECHNICAL FIELD

The invention relates to systems and methods for context-linked importation of user information. Embodiments of invention are particularly applicable to interactive environments such as message boards.

BACKGROUND OF THE INVENTION

The advent of the World Wide Web offers new opportunities for people to share information, opinions, and experiences on virtually any topic. With the support of web-based systems and methodologies, people with common goals and interests can interact and communicate instantaneously from anywhere on the globe.

Many web sites exist to serve a particular group of people who share common goals or attributes. Such web sites often include message boards in which users can communicate with each other regarding various topics of interest.

Conventional message boards suffer from several deficiencies. For example, users have difficulty assessing the credibility and/or accuracy of other posts. Likewise, without face-to-face communication, users may lack context for a posting, particularly if the user joins in the middle of conversation.

Accordingly, there is a need for systems and methods for context-linked importation of user information.

SUMMARY OF THE INVENTION

Various aspects of the invention described herein provide systems and methods for context-linked importation of user information.

One aspect of the invention provides a method for context-linked importation of user information. The method includes: providing an interactive environment that allows posting of content by a plurality of pre-identified users; receiving content for the interactive environment from a pre-identified user; selecting relevant data about the pre-identified user from a database, the relevant data selected based on information contained in the content; and displaying the relevant data along with the content on the interactive environment.

This aspect of the invention can have a variety of embodiments. The method can include updating the database with information contained in the content. The database can be a topic-related database. The topic can relate to health.

The relevant data can include at least one medical condition metric. The medical condition metric can be a quantitative representation of a medical condition. The medical condition metric can be one selected from the group consisting of: a direct measure of pathology, a user-reported measure of functional impairment, a user-reported outcome of health-related quality of life, and a user-reported progression of a medical condition.

The medical condition can be one selected from the group consisting of: movement disorders including parkinsonism, Huntington's chorea, and Tourette's syndrome; pain disorders including back pain; rheumatologic disorders including arthritis, osteoarthritis, rheumatoid arthritis, psoriatic arthritis, Lyme's disease, and gout; seizure disorders including epilepsy; neurodegenerative diseases including amyotrophic lateral sclerosis, multiple sclerosis, Creutzfeld-Jakob disease, and Alzheimer's disease; pulmonary diseases including asthma, chronic obstructive pulmonary disease, and cystic fibrosis; sexual disorders including erectile dysfunction and vaginismus; mood disorders including depression and anxiety; addiction including nicotine addiction and alcoholism; migraines; fibromyalgia; fatigue disorders; dementia; eating disorders; hypercholesterolemia; hyperlipidemia; hyperlipoproteinemia; hypertriglyceridemia; vasculatitis, diabetes; obesity; gastroesophogeal reflux disorder; dyspepsia; anemia; cancer; hypertension; renal failure; lupus; pregnancy; and post-operative conditions.

The relevant data can include intervention data. The intervention data can include at least one selected from the group consisting of: intervention dosage, intervention frequency, and intervention adherence. The intervention data can be data about an intervention selected from the group consisting of: administration of a medication, administration of a remedy, administration of a nutritional supplement, administration of a vitamin, exercise, physical therapy, massage, stretching, consumption of food, rest, and sleep.

The method can further include providing an interface for the user to submit new data about an intervention or medical condition metric. The new data can be displayed along with the post on the interactive environment.

The relevant data can be displayed in a graphical element. The graphical element can be a chart. The chart can be a line chart. Time can be depicted on an x-axis of the chart. The method can be a computer-implemented method.

The method can include the steps of: receiving a response from a second pre-identified user; selecting relevant data about the second pre-identified user from a database, the relevant data about the second pre-identified user selected based on information contained in the response; and displaying the relevant data about the second pre-identified user along with the response on the interactive environment.

The method can include providing an interface for the user to submit new data about an intervention or medical condition metric. The method can include displaying the new data along with the post on the content board. The method can include displaying hyperlinks to additional information about a subject of the content along with the content.

Another aspect of the invention provides a computer-readable medium whose contents cause a computer to perform a method for context-linked importation of user information. The method includes: providing an interactive environment that allows posting of content by a plurality of pre-identified users; receiving content for the interactive environment from a pre-identified user; selecting relevant data about the pre-identified user from a database, the relevant data selected based on information contained in the content; and displaying the relevant data along with the content on the interactive environment. The computer-readable medium can be non-transitory and tangible.

Another aspect of the invention provides a system for the context-linked importation of user information. The system includes: a database; and a server in communication with the database. The server is configured to provide an interactive environment that allows posting of content by a plurality of pre-identified users, receive content for the interactive environment from a pre-identified use, select relevant data about the pre-identified user from a database, and display the relevant data along with the content on the interactive environment. The relevant data is selected based on information contained in the content.

Another aspect of the invention provides a system for the context-linked importation of user information. The system includes a messaging module and a data importation module. The messaging module is configured to provide an interactive environment that allows posting of content by a plurality of pre-identified users, receive content for the interactive environment from a pre-identified user, and display relevant data along with the content on the interactive environment. The data importation module is configured to select relevant data about the pre-identified user from a database based on information contained in the content. The system can include an authentication module configured to authenticate the pre-identified user.

Another aspect of invention provides a method for context-linked importation of user information. The method includes providing an messaging system that allows transmission of content between a plurality of users, wherein at least one of the users is pre-identified, receiving content from a first, pre-identified user to a second user, selecting relevant data about the pre-identified user from a database, the relevant data selected based on information contained in the content; and presenting the relevant data along with the content to the second user.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views and wherein.

DEFINITIONS

Figure 1:
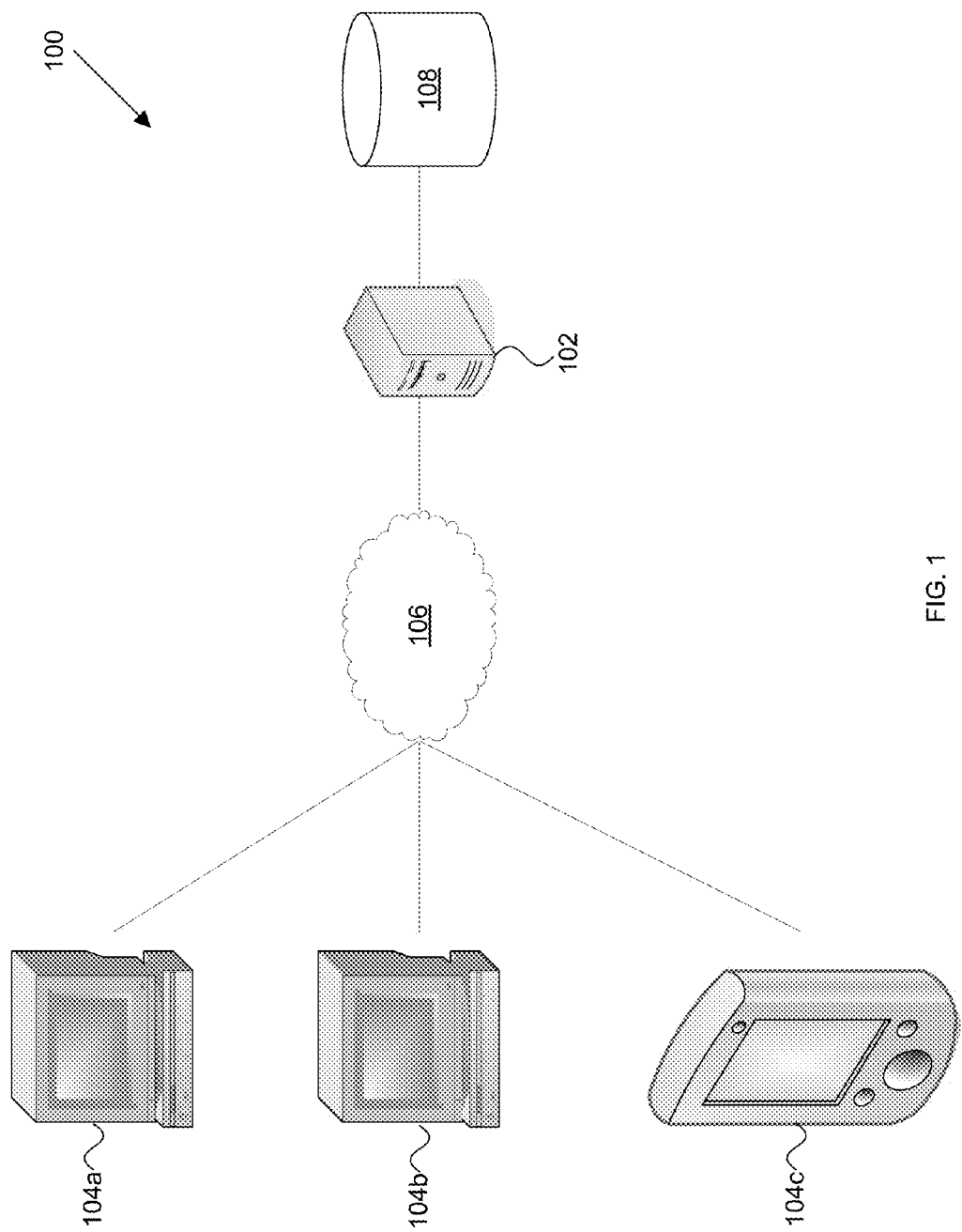
FIG. 1 depicts an exemplary network topology according to the invention.

The instant invention is most clearly understood with reference to the following definitions:

As used in the specification and claims, the singular form "a," "an," and "the" include plural references unless the context clearly dictates otherwise.

The term "disease" refers to an abnormal condition of an organism that impairs bodily functions. The term disease includes a variety of physical ailments including, but not limited to, neurological diseases (e.g., Amyotrophic Lateral Sclerosis (ALS), Multiple Sclerosis (MS), Parkinson's Disease), Human Immunodeficiency Virus (HIV), Acquired Immune Deficiency Syndrome (AIDS), cancers (e.g., bladder cancer, blood cancer, breast cancer, colorectal cancer, endometrial cancer, leukemia, lung cancer, lymphoma, ovarian cancer, pancreatic cancer, prostate cancer, and skin cancer), diabetes, digestive disorders (e.g., irritable bower syndrome, gastro esophageal reflux disease, and Crohn's Disease), cardiovascular diseases, osteoporosis, chronic obstructive pulmonary disease (COPD), arthritis, allergies, geriatric diseases, and autoimmune diseases (e.g., lupus). The term disease also include mental ailments including, but not limited to, depression, anxiety disorders, post traumatic stress disorder, mood disorders, psychotic disorders, personality disorders, and eating disorders.

The term "medical condition" refers to a manifestation of a disease such as a symptom. For example, if a patient suffers from Amyotrophic Lateral Sclerosis (ALS), the patient may experience one or more medical conditions such as dysphagia (impaired swallowing).

The term "intervention" refers any event that has a positive, negative, or neutral effect on one or more medical conditions. The term intervention includes a variety of activities including, but not limited to, administration of a medication, administration of a remedy, administration of a nutritional supplement, administration of a vitamin, exercise, physical therapy, massage, stretching, consumption of food, rest, and sleep.

The term "thread" refers to a chain of messages, postings, or the like, which follows one or more chosen topics.

The term "interactive environment" refers to any construct in which a plurality of users can interact. Exemplary interactive environments include, but are not limited to, thread-based forums such as message boards, answer-based forums, wilds, web logs (also known as "blogs"), micro-blogs (e.g., TWITTER®, available from Twitter, Inc. of San Francisco, Calif.), social networking sites (e.g., FACEBOOK®, available from Facebook, Inc. of Palo Alto, Calif., LINKEDIN®, available from LinkedIn, Ltd. of Mountain View, Calif., and the like), and private messages (e.g., electronic mail).

DETAILED DESCRIPTION

Various aspects of the invention described herein provide systems and methods for context-linked importation of user information. Aspects of the invention are particularly applicable to interactive environments such as message boards (also known as Internet forums, online discussion sites, bulletin boards, and the like). Aspects of the invention are also applicable to other varieties of Internet applications.

In general, aspects of the invention integrate aspects of a user's background and/or history and associate relevant data from the user's background and/or history with a posting by the user.

Referring to FIG. 1, an exemplary network topology 100 for an interactive environment (e.g., a message board) is depicted. The message board is hosted on server 102, which is in communication with clients 104a-c via network 106.

The terms "client" and "server" are used to reflect a client-server relationship between elements 102 and 104a-104c. Suitable devices for server element 102 include, but are not limited to general-purpose computers, including, but not limited to computers with higher processing power colloquially known as "servers." Likewise, suitable devices for client elements 104a-104c include, but are not limited to general-purpose computers, including, but not limited to desktop computers, laptop computers, tablet computers, personal digital assistants, cellular telephones, smartphones, video game systems, digital video recorders (DVRs), and the like.

Clients 104 can interact with one or more peripheral devices (not depicted). Such peripherals can include conventional peripherals such as cameras, microphones, and the like as well as medical device such as insulin pumps, pacemakers, and the like. Client 104 can interact with peripherals using a variety of wired or wireless standards.

Suitable wired standards include Universal Serial Bus (USB), USB 2.0, IEEE 1394, Peripheral Component Interconnect (PCI), Ethernet, Gigabit Ethernet, and the like. The USB and USB 2.0 standards are described in publications such as Andrew S. Tanenbaum, *Structured Computer Organization* §3.6.4 (5th ed. 2006); and Andrew S. Tanenbaum, *Modern Operating Systems* 32 (2d ed. 2001). The IEEE 1394 standard is described in Andrew S. Tanenbaum, *Modern Operating Systems* 32 (2d ed. 2001). The PCI standard is described in Andrew S. Tanenbaum, *Modern Operating Systems* 31 (2d ed. 2001); Andrew S. Tanenbaum, *Structured Computer Organization* 91, 183-89 (4th ed. 1999). The Ethernet and Gigabit Ethernet standards are discussed in Andrew S. Tanenbaum, *Computer Networks* 17, 65-68, 271-92 (4th ed. 2003).

Suitable wireless standards include Bluetooth, IEEE 802.11, IEEE 802.15.4, and the like. The Bluetooth standard is discussed in Andrew S. Tanenbaum, *Computer Networks* 21, 310-17 (4th ed. 2003). The IEEE 802.11 standard is discussed in Andrew S. Tanenbaum, *Computer Networks* 292-302 (4th ed. 2003). The IEEE 802.15.4 standard is described in Yu-Kai Huang & Ai-Chan Pang, "A Comprehensive Study of Low-Power Operation in IEEE 802.15.4," in *MSWiM '07* 405-08 (2007).

Network 106 can be any network capable of transmitting data between clients 104a-104c and server 102, for example, an intranet or the Internet.

The server can be in communication with a database 108. Database 108 can be operated through a database management system (DBMS). A DBMS is imposed upon data to form a logical and structured organization of the data. A DBMS lies between the physical storage of data and the users and handles the interaction between the two. Examples of DBMSes include DB2® and INFORMIX® both available from IBM Corp. of Armonk, N.Y.; MICROSOFT JET® and MICROSOFT SQL SERVER® both available from the Microsoft Corp. of Redmond, Wash.; MYSQL® available from the MySQL Ltd. Co. of Stockholm, Sweden; ORACLE® Database, available from Oracle Int'l Corp of Redwood City, Calif.; and SYBASE® available from Sybase, Inc. of Dublin, Calif.

Figure 2A:
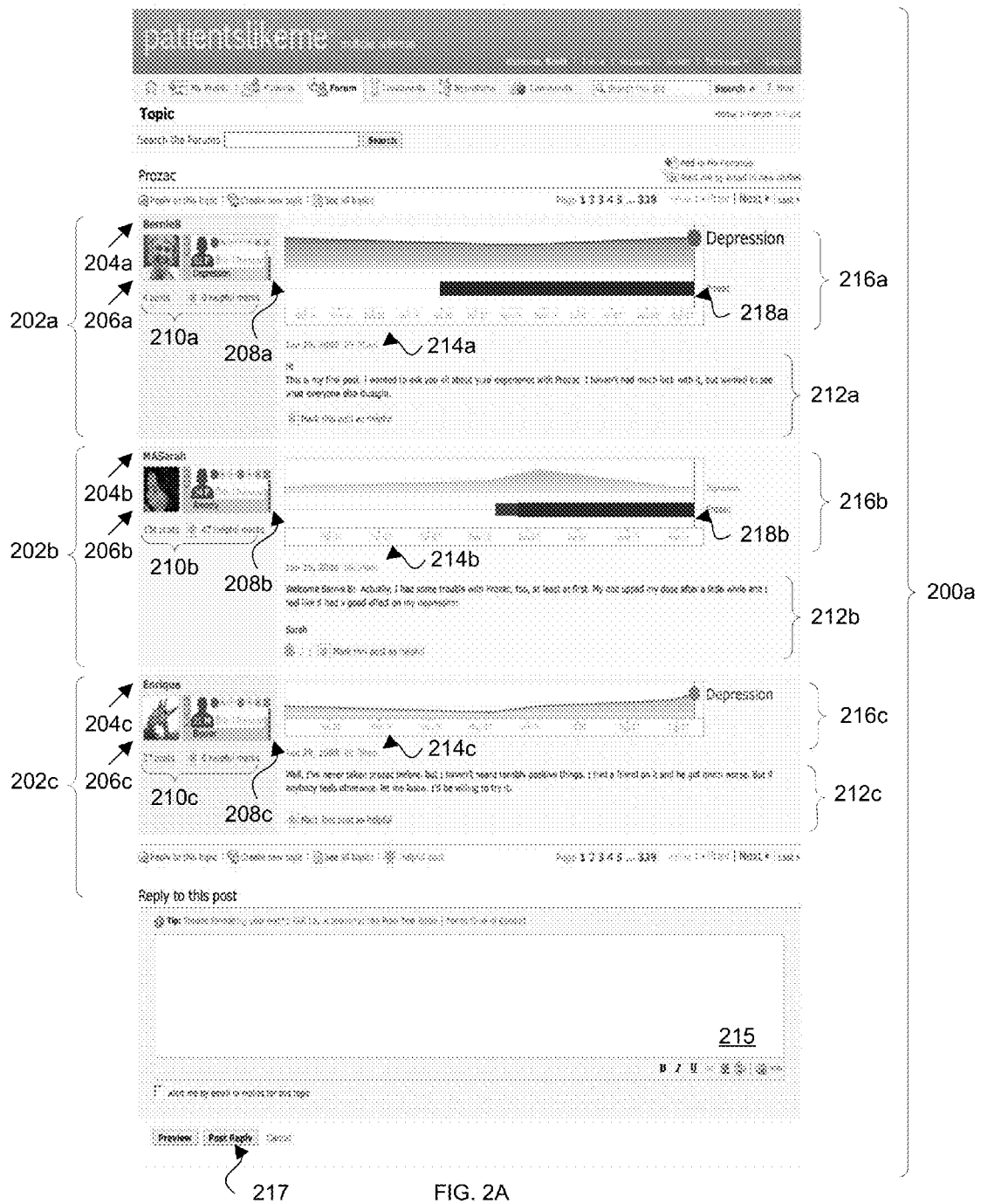
FIGS. 2A and 2B depict the operation of an interactive environment according to embodiments of the invention.

Referring to FIG. 2A, the operation of an interactive environment (e.g., a message board) is depicted. A user interface 200a is provided to one or more users. The user interface 200a can be provided via an Internet browser such as INTERNET EXPLORER®, available from Microsoft Corporation of Redmond, Wash.; FIREFOX®, available from the Mozilla Foundation of Mountain View, Calif.; OPERA®, available from Opera Software AS of Oslo, Norway; or CHROME™, available from Google Inc. of Menlo Park, Calif. Alternatively, the user interface 200a can be provided via specially-programmed software, such as an application installed on clients 104a-104c.

The user interface 200a includes one or more postings 202a-202c. These postings 202a-202c were previously transmitted to the server by users. Each posting 202a-202c can include information about the author of the posting 202a-202c. For example, the postings 202a-202c can display user name 204a-204c and/or a picture, icon, or avatar 206a-206c associated with the author of the posting 202a-202c. Each posting 202a-202c can also display other information about the author such as age, gender, disease, remedies, and the like. Such information can be represented graphically in a mosaic 208a-208c as depicted in FIG. 2a. The posting can also display information 210a-210c about the author's posting history such as the number of posts and number of postings by the author that were designated "helpful" by other users.

Postings 202a-202c can also contain user-posted content 212a-212c. For example, in posting 202a in FIG. 2, user "BernieB" inquires about other users' experience with PROZAC® (fluoxetine hydrochloride). User-posted content 212a-212c can include any combination of media including text, audio, video, graphics, emoticons, and the like. The postings 202a-202c can include a time-stamp 214a-214c indicating when the posting was submitted.

One or more users can respond to posting 202a by a user by entering content in field 215 and pressing the "Post Reply" button 217. This reply is added to the message board one or more users to view. For example, as depicted in postings 202b and 202b in FIG. 2, users "MASarah" and "Enrique" provide commentary on their experiences and the experiences of others with PROZAC®.

The invention herein allows for the context-linked importation of user information into a message board. The message board is associated with one or more databases containing information about a plurality of users.

The stored information can include one or more medical condition metric. A medical condition metric can be a qualitative or quantitative metric related to a medical condition. For example, a medical condition metric can be a qualitative measure of an Amyotrophic Lateral Sclerosis (ALS) patient's feeling of well-being at a particular time of day. The patient may feel great, good, fair, poor, or awful at a particular time of day due to the symptoms and treatments for ALS, and daily activities such as eating and exercising that interact with and affect his condition. Alternatively, the metric can be quantitative in nature, such as blood pressure (e.g., for a patient with heart disease), blood test values (e.g., sodium, potassium, chloride, bicarbonate, blood urea nitrogen, magnesium, creatinine, glucose, calcium, cholesterol, carbon dioxide, oxygen, hematocrit), pulse, temperature, T-cell count, and the like.

Various rating scales exist to measure medical conditions. In addition to discrete scales such as asking whether the patient feels great/good/fair/poor/awful, numerical scales can be used which ask the patient to quantify one or aspects of their medical condition, for example, on a 1-10 numerical scale. The metric can be a composite metric that produces a numerical representation of the condition based on a series of measurements. Rating scales for measuring depression include the Beck Depression Inventory, the Hamilton Depression Ration Scale, and the Montgomery-Åsberg Depression Rating Scale. Rating scales for assessing ALS patients include the Appel ALS rating scale and the ALS Functional Rating Scale (ALSFRS). Rating scales for Parkinson's Disease include the Unified Parkinson's Disease Rating Scale (UPDRS).

The medical condition metrics for a given user can be associated with a particular time. For example, a user may report that the severity of her depression is a '7' on a scale from 1-10 at 9:00 AM on Jan. 1, 2009. A plurality of associated medical condition metrics and time data can be utilized to produce a chart 216a-216c (e.g., a line chart) as depicted in FIG. 2.

Still referring to FIG. 2, charts 216a-216c can include information 218a, 218b about one or more interventions. Such information can include dosing information for a medication (e.g., time and date and quantity) and/or pharmacokinetic data regarding the concentration of a medication within the user over time.

The specific medical condition metric(s), intervention(s), and/or time frame can be selected to compliment a particular user's posting. For example, in posting 202a, user "BernieB" inquires about PROZAC®. Server 102 detects that the posting concerns PROZAC®, and includes information about the user's dosage history for PROZAC®. Server 102 can also infer that user's posting relates to depression. This inference can be drawn based on a number of factors. For example, the user can be posting in a forum relating to depression. In another example, server 102 consults a resource such as the *Physicians' Desk Reference* or the EPOCRATES® database (available from Epocrates, Inc. of San Mateo, Calif.) to determine prescribing information for PROZAC® (i.e., what indications PROZAC® is approved for). In yet another example, server 102 mines existing user information to detect "off-label" uses of various medications by other patients.

Figure 2B:
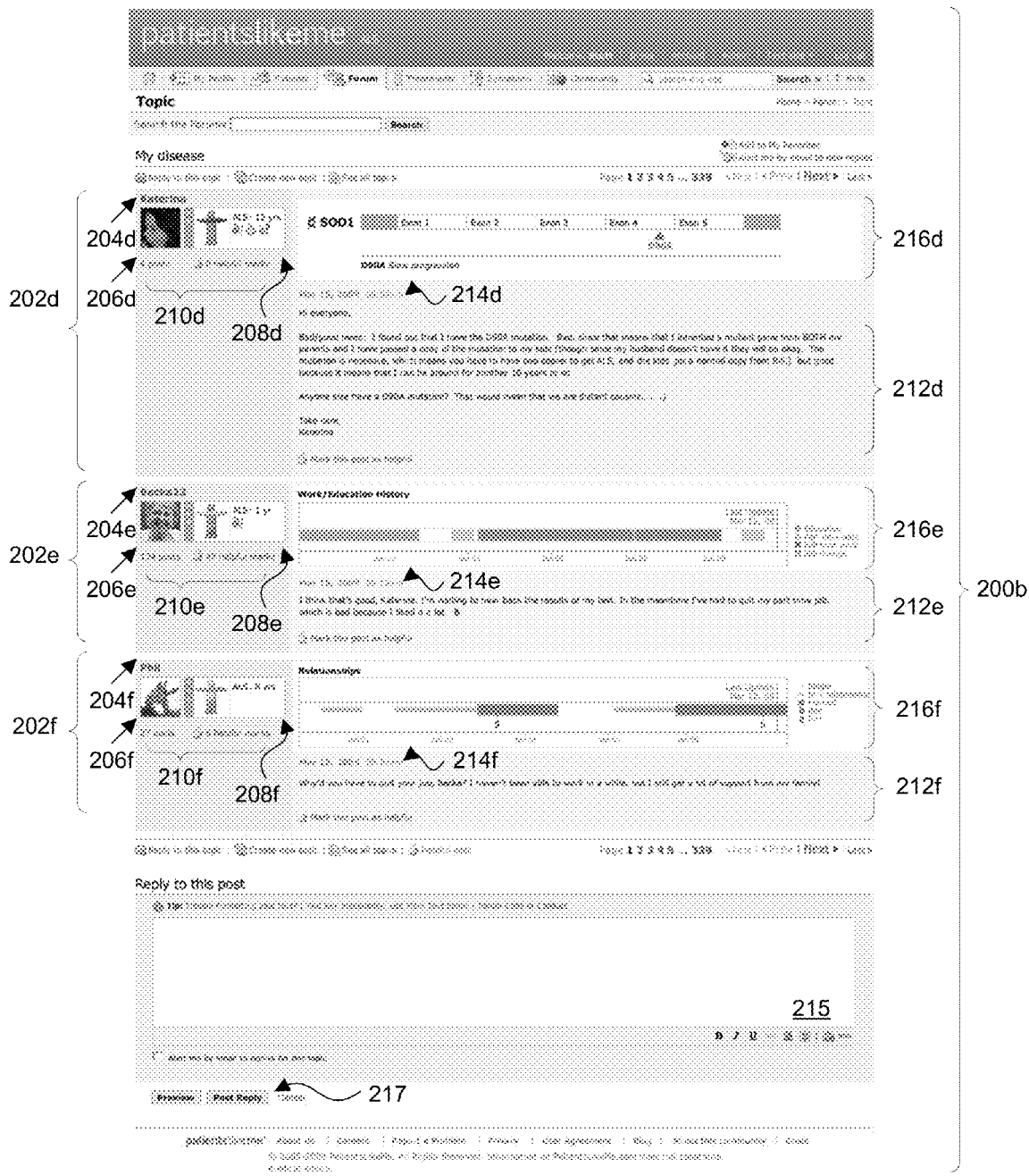

Referring now to FIG. 2B, a variety of other information can be displayed along with postings 202. For example, in posting 202d, the user-posted content 212d for user "Katerina" states that she has the D90A mutation. Chart 216d is a schematic showing the location of the D90A mutation on the SOD1 gene.

In posting 202e, the user-posted content 212e for user "Katerina" states that that she recently quit her part-time job. Chart 216e is a line chart depicting the user's work history. Various color-coded bars and symbols denote periods where the user was enrolled in an educational program, held a full-time job, and held a part-time job.

In posting 202f, the user-posted content 212f for user "Phil" states that he has received support from his family. Chart 216f is a line chart displaying the user's relationship status. Color-coded bars of various thicknesses and symbols denote periods where the user was single, in a relationship, married, and when the user's children where born.

A variety of other information can be imported and displayed based on the user-posted content 212 in a posting 202. For example, if the user-posted content 212 discusses the user's deployment as part of Operation Enduring Freedom—Afghanistan, chart 216 may be a line chart representing the user's deployment history. Relevant information can include rank, unit, combat status, and the like. In another example, if the message board is of an academic nature, relevant publications or portions of the user's curriculum vitae can be imported into the posting 202 based on the user-posted content 212. Additionally, articles or portions of articles (e.g., an abstract) can be imported from variety of sources (e.g., PUBMED®, available from The National Library of Medicine of Bethesda, Md.; or THE NEW YORK TIMES®, available from The New York Times Company of New York, N.Y.) and displayed in the thread. Other media such as blogs, microblogs (e.g., TWITTER®, available from Twitter, Inc. of San Francisco, Calif.), annotations, status updates (e.g., on a social networking site such as FACEBOOK®, available from Facebook, Inc. of Palo Alto, Calif.), and the like can also be imported and displayed in the thread.

The invention can also display one or one or more charts 216 displaying a variety of data relevant to posting. For example, if the user-posted content 212 discusses lung cancer, a chart 218 can be produced containing information about the user's environmental exposure (e.g., employment in a plant containing asbestos), the user's family history (e.g., in a family tree including information about cancer in user's ancestors), and the user's genetic profile. Other environmental factors can include weather information such as temperature, barometric pressure, precipitation, sunlight, and the like. Other external data can be included such as the user's location, financial data (e.g., the performance of financial markets as reflected in indexes such as the S&P 500® index available from Standard & Poor's Corporation of New York, N.Y.), and the like. Such external data can be particularly tailored to an individual user. For example, a user can make available information about her portfolio so that individualized financial data or an abstraction thereof can be presented along with information on the user's condition.

The system can include privacy settings that allow a user to control how private information (e.g., medical history, financial history, and the like) is utilized. Users can restrict all or certain information from being utilized in various manners. For example, a user can allow all of their data to be used to compute aggregate data, but restrict the viewing of certain data in the context of the particular user.

By viewing a chart 216 with relevant user information, other users have additional context for viewing the user's posting 202. For example, users can observe that BernieB's depression has not improved since commencing PROZAC®. Moreover, other users can observe the duration and dosing level for user "BernieB" and provide commentary based on their dosing experiences. For example, if a patient commented that PROZAC® was not improving his depression, another user might observe from the chart that the user has only taken PROZAC® for two weeks, which can be an insufficient time to achieve a stable concentration in the user's body and comment accordingly.

Additionally, the incorporation of relevant user information can counter any memory bias by the poster. Presumably, users will have minimal, if any, motivation to exaggerate medical condition metrics as they experience them. Therefore, this data can serve to verify whether the user's recollection in a posting 202 is accurate, thereby enhancing the credibility of accurate postings 202 and calling into question inaccurate postings 202.

Referring again to FIG. 2A, chart 216b in posting 202b confirms the poster's increased dosage of PROZAC®, which is represented by a thicker line along the bottom of chart 216b, and the corresponding improvement in the user's depression, which is represented by the downward slope of the line graph.

Additionally or alternatively, the interactive environment can display information about the medical condition and/or intervention along with the posting. For example, a message board can include links to information about depression and/or PROZAC® from sources such as the Centers for Disease Control and Prevention, WebMD® services, the *Physicians' Desk Reference*, the EPOCRATES® database, and the like.

The charts 216 can be interactive. For example, a user can modify the visible time range of the chart 216. Likewise, the user can hide one or more charts 216 or chart components. A user can also "drill down" to view additional chart components or the underlying data for chart 216, for example by clicking on chart 216.

The visible time range can initially be calculated based on information in the message thread and/or the user viewing the thread. For example, if the postings in the thread refer to the user's change in depressive symptoms during the winter, each chart 216 can be configured to display a medical condition metric during the winter months. In another alternative, the user asks about other users' experiences with PROZAC®. The charts 216 can be configured to display medical condition metrics for the period after each user began taking PROZAC®.

User interactions with charts 218 can be stored and mined to rank the posting 202 and/or refine the chart. For example, frequent clicks on chart 218 may indicate that chart is interesting to many users, which can result in the prominent display of the posting 202. Likewise, if a user views a chart 218 for a significant period of time, the posting may be interesting to many users. In contrast, if many users hide the chart 218 or spend little time viewing the chart 218, the posting 202 may be less interesting, resulting in a less prominent display.

Users can also indicate the helpfulness of a posting 202 and/or chart through or more buttons and/or other GUI elements in interface 200.

An aggregate chart can be displayed for a message thread. The aggregate chart can include a plurality of sets and or average data for all users that made postings 202 in a thread. Such an aggregate chart can provide valuable context about the nature of the user's medical condition vis-à-vis other users in the thread.

Identification of Relevant Information

Relevant user information can be selected for importation in a variety of ways such as tagging or natural language processing. Relevant user information can be identified automatically (i.e. without the necessity of human involvement).

In a tagging method, one or more users can identify one or more relevant terms in the user-posted content 212. This can occur in several ways. For example, user can select one or more terms in the user interface 200 and press a button to tag the one or more terms as "relevant." Additionally or alternatively, one or more administrators and/or moderators can tag relevant terms. Terms can be tagged as relevant by the author of the posting 202 or another user. More than one term can be tagged in each posting 202.

Figure 3:
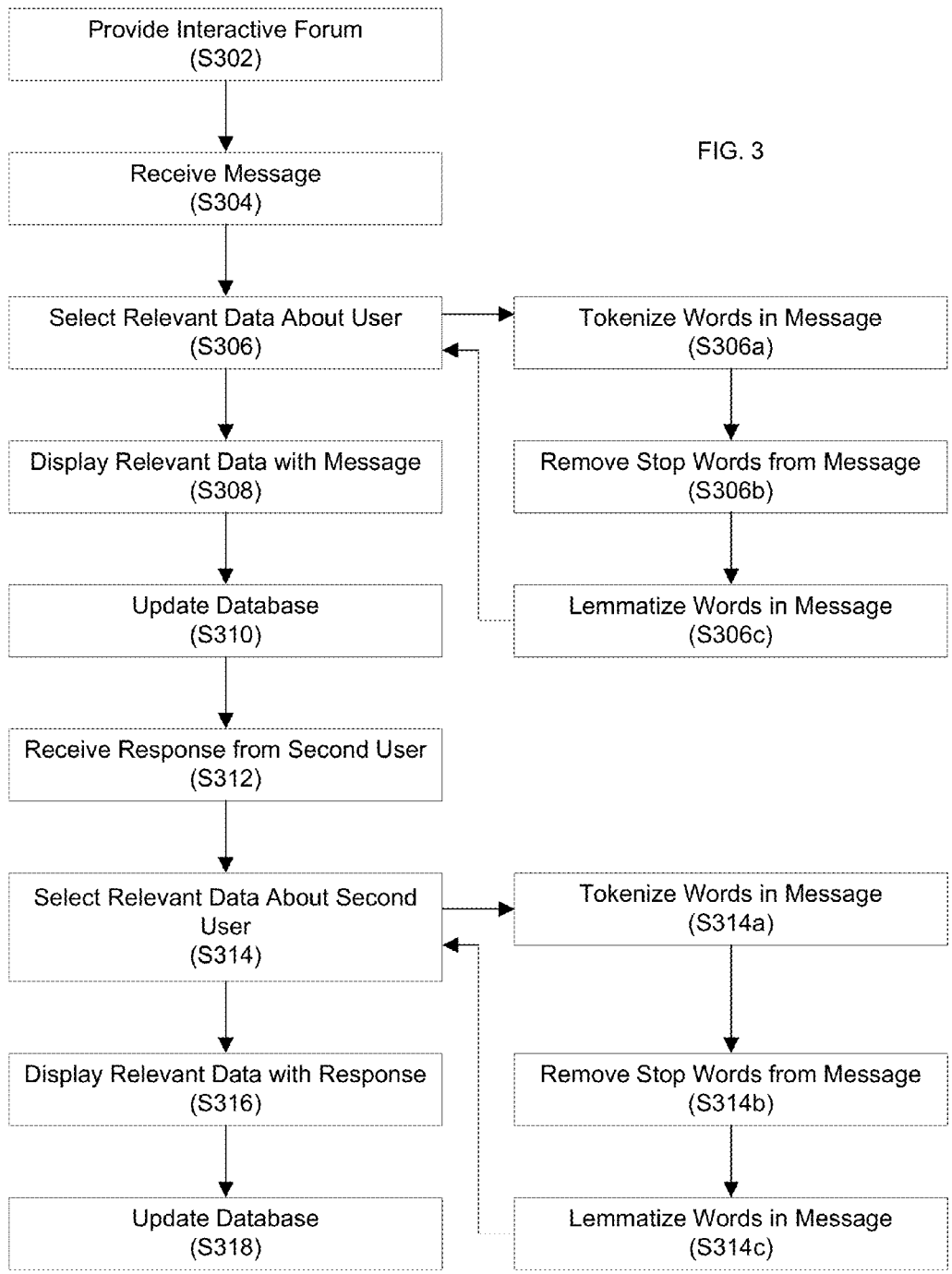
FIG. 3 depicts a method for context-linked importation of user information according to one embodiment of the invention.

In contrast, FIG. 3 depicts a method for context-linked importation of user information through natural language processing. Such a method can be implemented, for example, on server 102 as described herein. In step S302, an interactive environment (e.g., a message board) is provided. In step S304, a message (e.g., a posting) is received from a pre-identified user.

Users can be pre-identified through a variety of means known to those of skill in the art. For example, users can enter a username and password when accessing the interactive environment. In another example, a persistent object such as a cookie in conventional Internet architectures and/or Local Stored Objects (LSOs) in FLASH® or AIR® platforms is stored on clients 104a-104c and act as an identifier. Cookies are described in H. M. Deitel et al., *Internet & World Wide Web: How to Program* 1060-68 (2000). The FLASH® or AIR® software platforms are available from Adobe Systems Incorporated of San Jose, Calif.

In step S306, relevant data about the pre-identified user is selected. In some embodiments, relevant data is selected based on contextual information mined from the message using preprocessing steps 306a-306c. Preprocessing maps a report onto a list of tokens that have linguistic meaning, i.e., words. Preprocessing can include one or more of the following steps: tokenization (S306a), stop word removal (S306b), and lemmatization (S306c).

Tokenization (S306a) separates punctuation from words.

Stop words (also called "stopwords" or "noise words") are common words that appear in too many messages and therefore do not have discriminative power. That is, stopwords cannot be used to capture the essence of a message such that one can differentiate one message from another. Standard lists of stop words are provided in software programs such as the SMART Information Retrieval System, available from Cornell University of Ithaca, N.Y. The SMART stop word list is available at ftp://ftp.cs.cornell.edu/pub/smart/english.stop. A collection of stopwords for a particular set of documents can be created by selecting the words that occur in more than 80% of existing messages. See R. Baeza-Yates & B. Ribeiro-Neto, *Modern Information Retrieval* §7.2 (1999).

Lemmatization (S306b) maps each morphological variation of a word to its base form. For example, the words, "go", "going", "went", and "gone" are lemmatized to "go", their root or base form. Suitable lemmatizers include the WORD-NET® system, available from Princeton University of Princeton, N.J. Other lemmatizers can be used, including the MORPHA™ software described in G. Minnen et al., "Applied morphological processing of English," 7(3) *Natural Language Engineering* 207-23 (2001) and available at http://www.informatics.susx.ac.uk/research/groups/nlp/carroll/morph.html.

Once the message is preprocessed, relevant data can be selected based on the contextual information identified. For example, if "blood pressure" was identified as contextual data, data about the user's blood pressure history (e.g., a chart) can be selected.

In step S308, relevant data about the user is displayed along with the message.

In step S310, the database is updated with data from the message. For example, the user might state in the message that they achieved an FRS score of 25 today. This information can be extracted and added to the database in the same manner as if the user had entered the information directly.

In step S312, a response is received from another pre-identified user. In steps S314-S318, relevant data is extracted from the response. This relevant data can be used to (i) identify the author of the response, (ii) identify the subject(s) of the response, and/or (iii) retrieve relevant information from a database to be displayed and/or posted to the database in the same or similar manner as discussed above.

Figure 4:
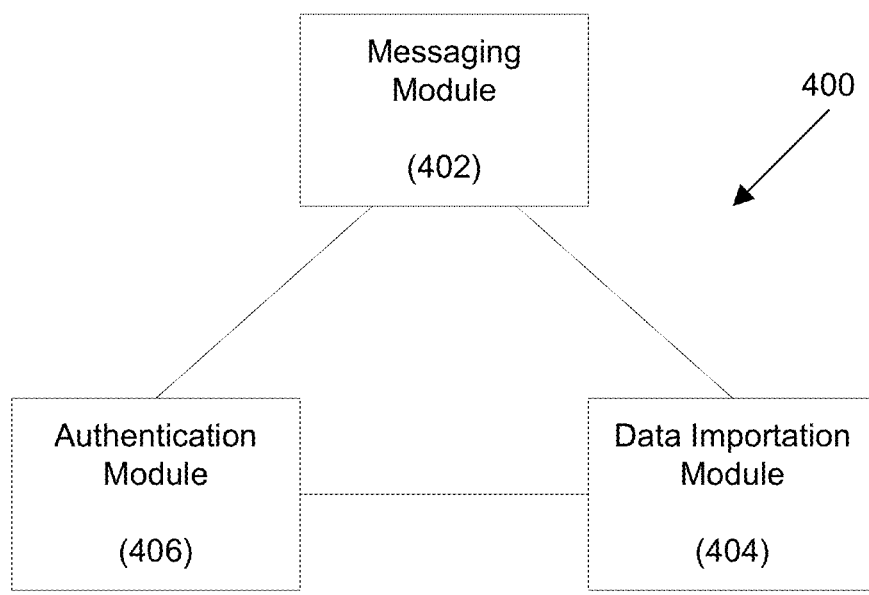
FIG. 4 depicts an embodiment of the invention in a computer software and/or hardware system.

Referring now to FIG. 4, the invention herein can be embodied in a computer software and/or hardware system 400. System 400 may contain one or more modules such as a messaging module 402, a data importation module 404, and/or an authentication module 406.

Messaging module 402 implements an interactive environment such as a message board. Accordingly, messaging module 402 can provide an interactive environment as described herein, receive messages for the interactive environment, and display relevant data along with the message on the interactive environment.

In order to enhance the flexibility and adaptability of system 400, messaging module 402 can communicate with data importation module 404. Data importation module 404 selects relevant data about a pre-identified user from the database based on information contained in the message as discussed herein, for example in FIG. 3 and associated text.

Messaging module 402 can also communicate with authentication module 406 to authenticate a pre-identified user. For example, messaging module 402 can pass a user name and/or password to authentication module 406, which then authenticates the user. Alternatively, authentication module 406 may maintain a persistent authentication of the user and confirm such authentication when requested by messaging module 402.

As will be appreciated by one of ordinary skill in the art, the modules 402, 404, 406 described herein can be implemented as components, i.e., functional or logical components with well-defined interfaces used for communication across components. For example, a system can be assembled by selecting a messaging component from several components (e.g., components that implement various approaches to message boards) and combining this component with a data importation component (e.g., a data importation module designed for a specific type of data and/or database) and an authentication component (e.g., an authentication component designed for a specific type of authentication).

Moreover, one of ordinary skill in the art will appreciate that the modules 402, 404, 406 described herein can be implemented using hardware, software, or a combination of hardware and software. For example, one or more modules can be implemented on one or more general purposes computer containing appropriate software to implement the invention as described herein.

Exemplary Data Entry User Interface

The interactive environment can include an interface that allows a user to enter data such as intervention data or medical condition metric data. This interface can be contained on the same page as a message board or can be accessible by a link or as a pop-up window.

Figure 5:
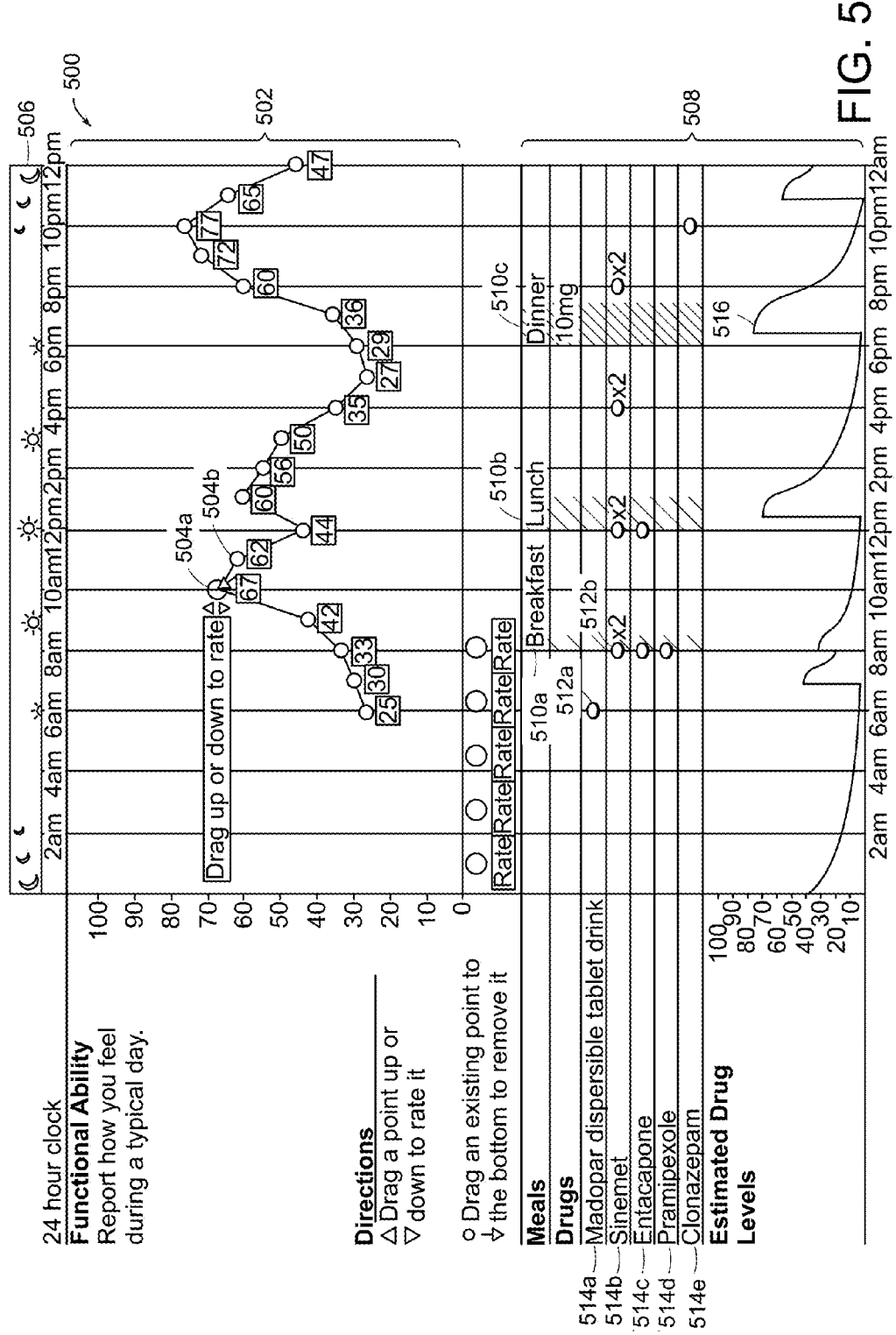
FIG. 5 depicts an exemplary user interface for data entry according to one embodiment of the invention.

Referring now to FIG. 5, an exemplary user interface 500 for data entry is provided. Although user interface 500 is illustrated as customized for a patient suffering from Parkinson's disease, the principles explained and depicted herein are equally applicable to any disease.

User interface 500 includes a medical condition metric portion 502, which allows the patient to input a medical condition metric (in this example, the patient's functional ability). The user can place multiple data points 504 in the medical condition metric chart, which includes a time scale. Data points 504 can be adjusted with respect to time and/or magnitude. For example, if the patient is indicating how she feels now or at a designated time, the patient can be limited to moving data point 504 up or down. Alternatively, the patient can input data for a time by dragging the data point to the left or right. The patient can be restricted from setting a data point in the future and/or the past.

User interface 500 also includes an intervention portion 508. Intervention portion 508 allows the patient to record one or more interventions such as administration of a medication, administration of a remedy, administration of a nutritional supplement, administration of a vitamin, exercise, physical therapy, massage, stretching, consumption of food, rest, and sleep. For example, the patient can designate when meals are eaten by adjusting bars 510a, 510b, 510c to indicate the beginning and ending of the meal. Likewise, the patient can indicate when one or more drugs 514a-514e are administered by placing markers 512 (which may depict pills) on a time scale.

Various types of remedies can be scheduled for specific times. For example, the patient can be prescribed to take MADOPAR™ (levodopa; benserazide hydrochl) at 6:00 AM. In this situation, user interface 500 can display a medication schedule. The patient can modify this schedule to reflect the actual administration by dragging marker 512a. Likewise, the patient can indicate that the drug was consumed by clicking on the marker 512a. Clicking on the marker can change the appearance of the marker 512a (e.g., its color) and thus can be used by patients, particularly patients with memory problems, to more faithfully follow a medication program.

User interface 500 can also include pharmacokinetic data, such as a pharmacokinetic curve 516 that depicts the concentration of a medication within the patient over time. Multiple pharmacokinetic curves 516 can be depicted in various colors or patterns to reflect varying pharmacokinetic properties of various medications. The pharmacokinetic curves can be generated using existing using formulas known to those of ordinary skill in the art.

Slider Bar

Figure 6A:
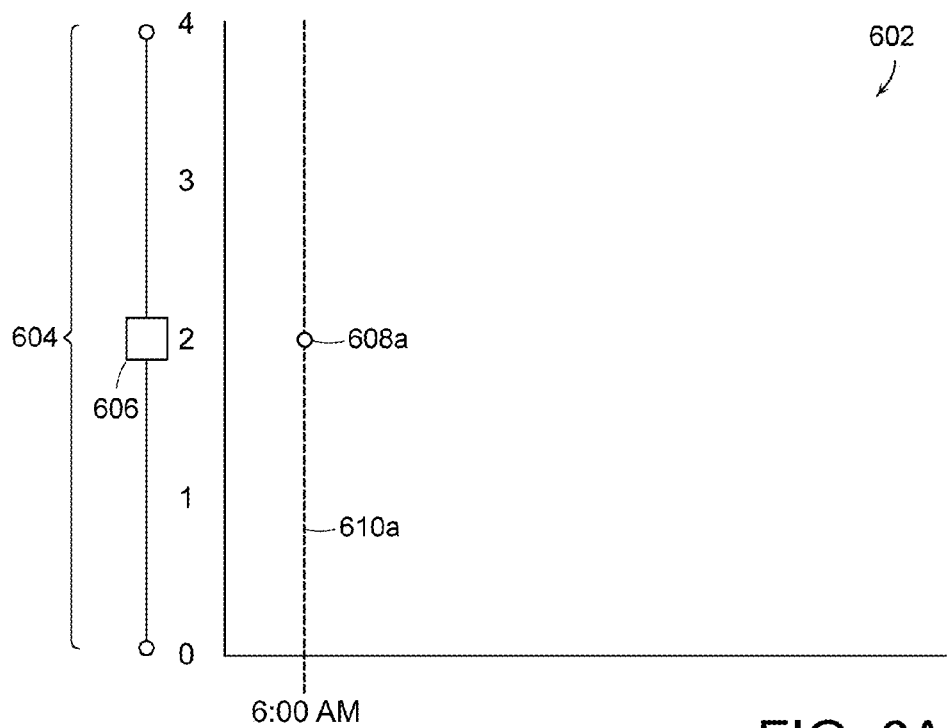
FIGS. 6A-6D depict an embodiment of a user interface for data entry according to one embodiment of the invention.

Referring to FIGS. 6A-6D, a user interface for data entry is provided. As in FIG. 5, a medical condition metric portion 602 is provided. In FIG. 6A, the first medical condition metric is recorded for a day. The patient either indicates that she wishes to record a metric from 6:00 AM or accesses the user interface at 6:00 AM, at which point the user interface can default to 6:00 AM. The patient manipulates slider bar 604 to input a medical condition metric. For example, if the patient wishes to indicate that '2' is the medical metric (e.g., a measurement of pain on a scale from 0-4), the user drags handle 606 of the slider bar 604 to the '2' position as depicted in FIG. 6A.

Data point 608a can move up and down along vertical line 610a as the handle 606 is moved or data point 608a may not appear until the medical condition metric is finalized A metric can be "finalized" in a number of ways, including by clicking the handle 606 to lock the handle 606. Additionally or alternatively, the metric can be finalized by a period of inactivity, for example, about fifteen seconds, about thirty seconds, and about one minute. In another alternative, data point 608a can also be moved left or right to modify the time associated with the data point.

As discussed in the context of FIG. 6A, the patient can indicate that he wishes to record metrics from 6:00 AM or can access the user interface at 6:00 AM at which point the user interface can default to 6:00 AM. The patient can leave the user interface open for a period of time and the patient can continue to access the user interface and manipulate the slider bar. Each time the user manipulates the slider bar 604, a new data point can be set for the time that the slider bar 604 is manipulated.

Figure 6B:
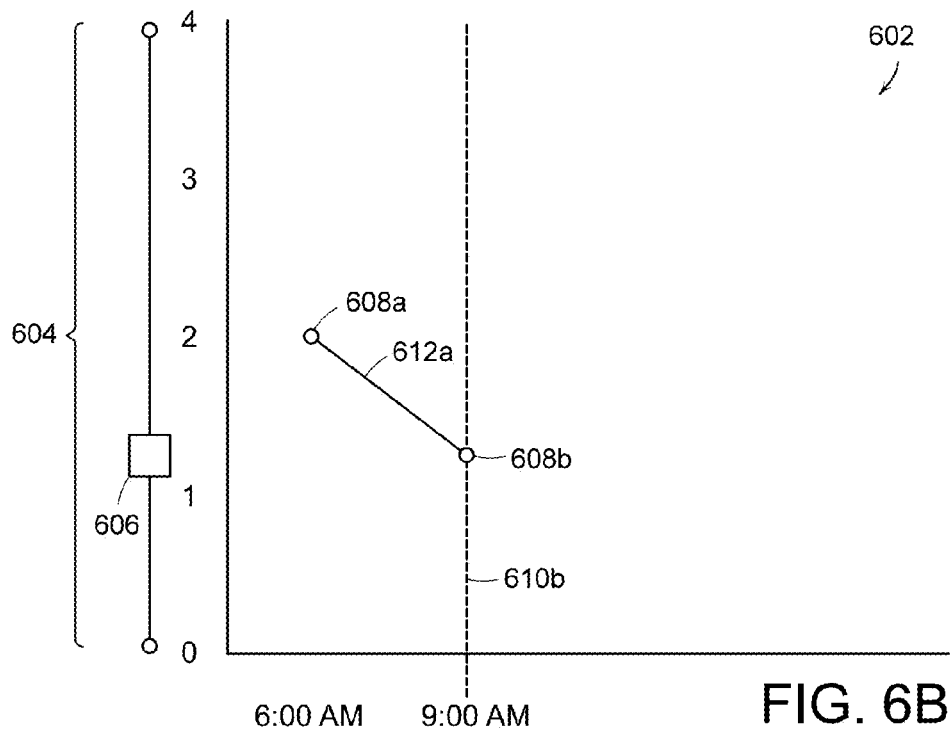
Figure 6C:
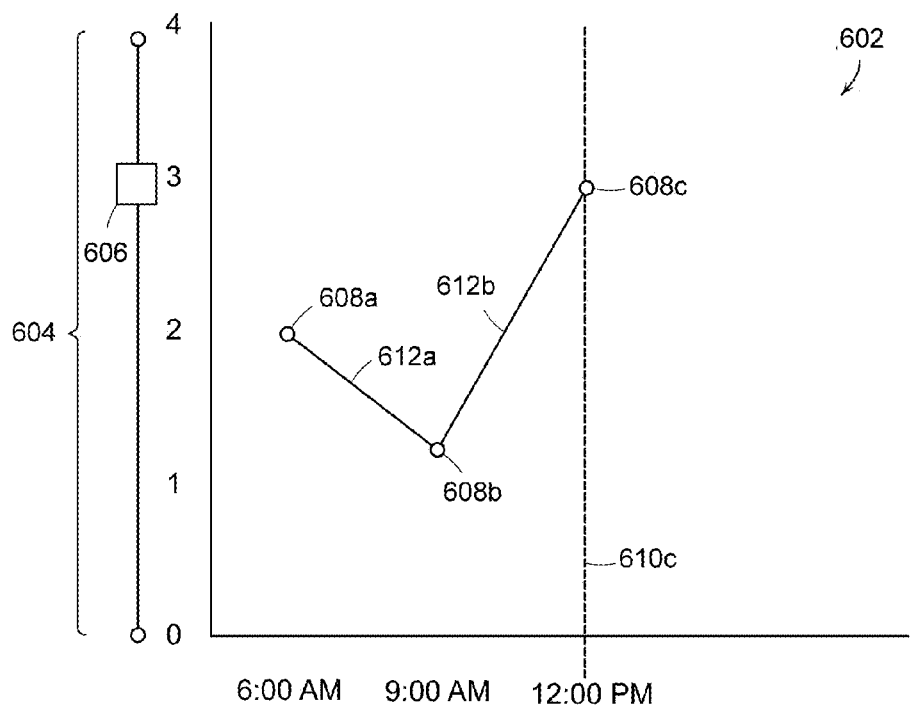

Referring now to FIG. 6B, the patient enters a second medical condition metric. The patient again moves the handle 606 of the slider bar 604. If the system is configured so that the data point 608b moves with the handle 606, line segment 612a also moves. Thus, the patient can readily see whether he is indicating that a medical condition metric is improving or deteriorating and verify that such a change truly reflects their experience.

Referring to FIG. 6C, the patient again manipulates the slider bar 604 to enter a third data point 608c and form a new line segment 612b.

Figure 6D:
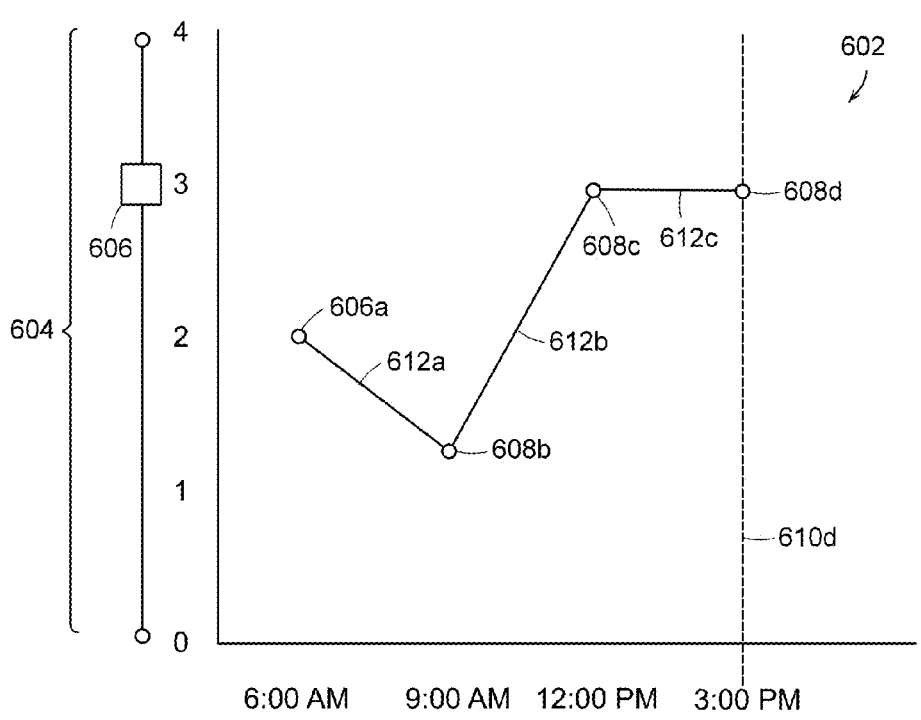

Referring to FIG. 6D, the patient indicates that the medical condition remains a '3' at 3:00 PM. The slider bar handle 606 remains at the '3' position from the 12:00 PM data entry. The patient can indicate that the metric remains a '3' by clicking on the handle 606 to lock the slider bar 604. During this, line segment 612c can grow horizontally from data point 608c as time progresses from 12:00 PM. Otherwise, the slider bar handle 606 can disappear after data point 608c is set. Handle 606 reappears when the patient clicks or moves the mouse over the slider bar 604.

Application of Invention to Other User-Generated Content

Although described in the context of an interactive environment, the invention is applicable to a variety of other applications. Specifically, user information can be selectively imported based on user-generated content other than postings to an interactive environment.

In one example, users send private messages to each other. Such private messages can be sent in real-time (analogous to instant messages) or can be sent and received asynchronously (analogous to email). User information (e.g., information about the sender or recipient) can be presented to the recipient along with the message.

In another example, a patient can communicate with their physician to request and/or refill a prescription. User information is selected based on the information in the request (e.g., the name of the prescription) and is presented to the physician along with the request.

Self-Updating Forums

Figure 7:
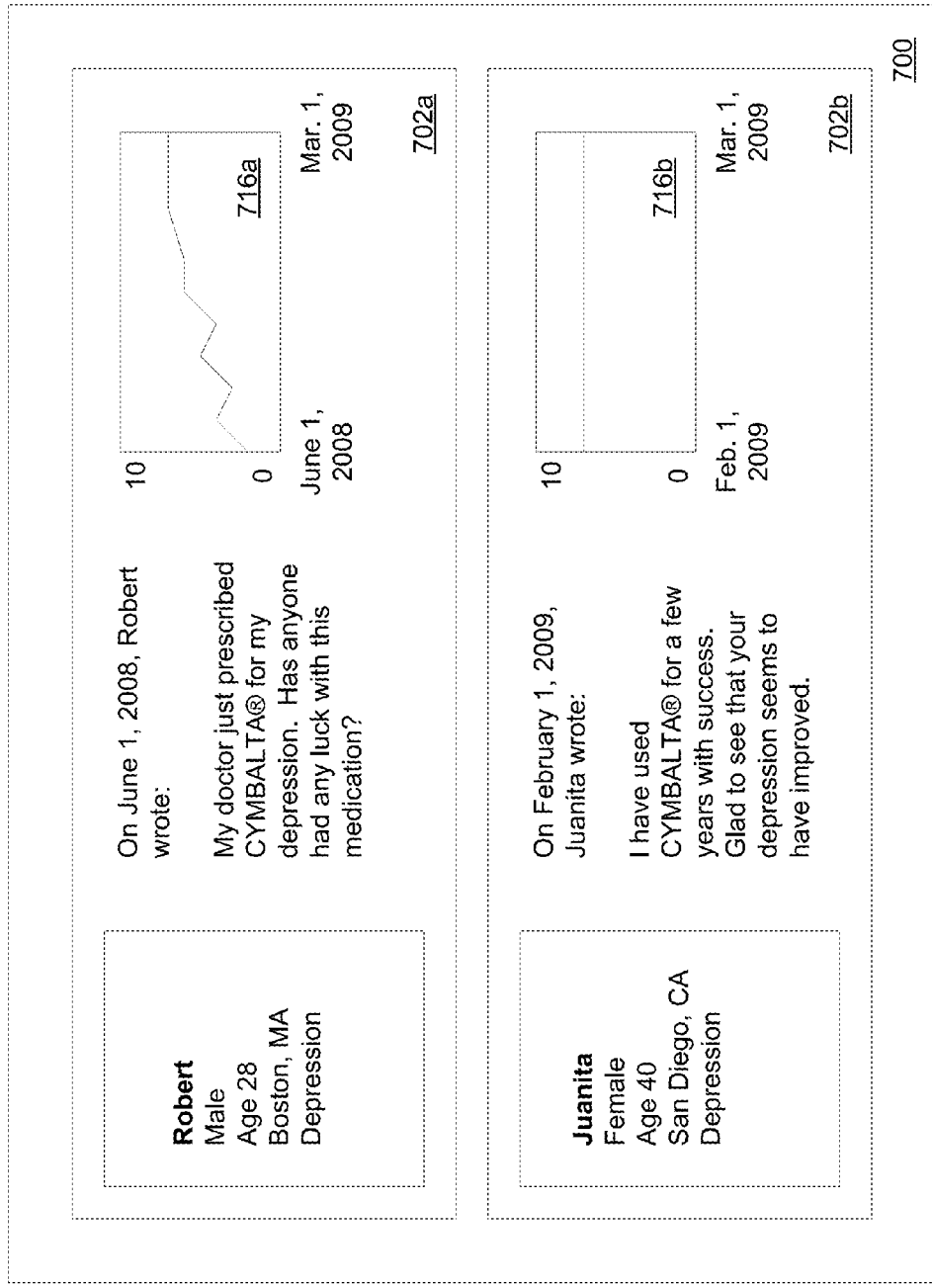
FIG. 7 depicts an embodiment of a self-updating forum according to one embodiment of the invention.

Referring now to FIG. 7, the invention provides a self-updating forum 700. In posting 702a, user "Robert" indicated that his doctor prescribed CYMBALTA® (duloxetine) for his depression.

Posting 702a includes a chart 716a. Chart 716a can be configured to display one or more metrics as discussed herein along an x-axis spanning between the date of the posting 702a and the current date (Mar. 1, 2009 in the example depicted in FIG. 7). Thus, any viewer can assess how the poster's condition has developed without the need for (i) the poster returns to the forum to add a further posting or (ii) the reader to locate any subsequent posting(s).

The ability of other users to view current information regarding the poster is reflected in posting 702b from user "Juanita" on Feb. 1, 2009. User "Juanita" viewed chart 716a (spanning from Jun. 1, 2008 to Feb. 1, 2009 at the time) and could visually appreciate that user Robert's condition had improved, as reflected in her posting 702b. Juanita's posting 702b also includes a chart 716b depicting her steady condition.

Incorporation in Blogs

Figure 8:
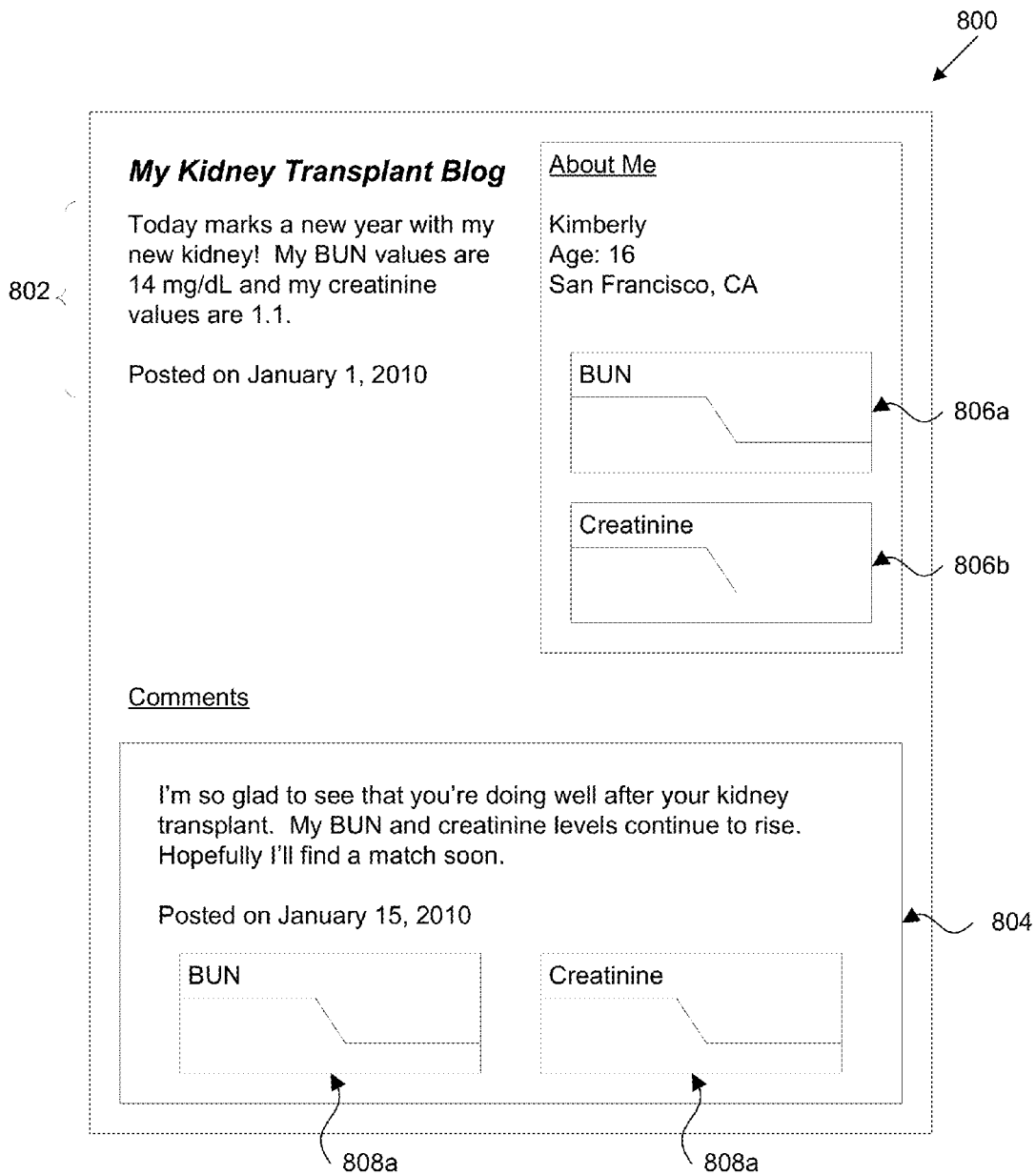
FIG. 8 depicts a blog incorporating an embodiment of the invention.

Referring now to FIG. 8, embodiment of the invention can be applied to web logs (commonly referred to as "blogs"). A user interface 800 of a blog can include a post 802 and one or more comments 804.

In the blog post 802, the author discusses her recent kidney transplant and discusses her BUN (blood urea nitrogen) and creatinine levels. Software mines the blog post for terms of interest such as BUN and creatinine, queries a database or other data source for relevant data, and generates one or more graphical elements 806a, 806b pertaining to the terms of interest in a similar manner to the methods described herein (e.g., method 300). In the example depicted in FIG. 8, graphs of the author's BUN and creatinine levels are depicted.

One or more readers can post comments 804 to the blog 800. Comments 804 can be mined for terms of interest in the same or similar manner as the blog post 802 and one or more graphical elements 808a, 808b can be associated with the comments 804.

INCORPORATION BY REFERENCE

All patents, published patent applications, and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Specifically, although this application periodically discusses the application of the invention to "diseases", the invention is equally applicable to other medical events such as aging, fertility, and the like. Moreover, the invention is not limited to medical events and conditions, but is applicable to other topics such as athletic training, weight loss, academic performance, financial management, and the like. Such equivalents are intended to be encompassed by the following claims.

The invention claimed is:

1. A method for context-linked identification and importation of user information from a database containing user information into an interactive environment implemented on a computer and accessible to other users via a network, the method comprising:
   providing the interactive environment on the computer that allows posting of content by a plurality of pre-identified users;
   receiving first content on the computer for the interactive environment from a first pre-identified user;
   automatically identifying and selecting on the computer relevant data about the first pre-identified user from a database based on the first content posted by the first pre-identified user, the relevant data selected from data previously-submitted by the first pre-identified user based on information contained in the first content posted by the first pre-identified user by:
      identifying one or more relevant terms for the first content by (i) performing natural language processing on the first content, (ii) parsing one or more tags applied to the first content, or (iii) forming an inference based on the first content; and
      selecting relevant data from the database based on the one or more relevant terms; and
   displaying via the computer the relevant data to other users along with the first content on the interactive environment.

2. The method of claim 1, further comprising:
   updating the database with information contained in the content.

3. The method of claim 1, wherein the database is a topic-related database.

4. The method of claim 3, wherein the topic relates to health.

5. The method of claim 4, wherein the relevant data includes at least one medical condition metric.

6. The method of claim 5, wherein the medical condition metric is a quantitative representation of a medical condition.

7. The method of claim 4, wherein the relevant data includes intervention data.

8. The method of claim 7, wherein the intervention data is selected from the group consisting of: intervention dosage, intervention frequency, and intervention adherence.

9. The method of claim 7, wherein the intervention data is data about an intervention selected from the group consisting of: administration of a medication, administration of a remedy, administration of a nutritional supplement, administration of a vitamin, exercise, physical therapy, massage, stretching, consumption of food, rest, and sleep.

10. The method of claim 1, further comprising:
    providing an interface for the first pre-identified user to submit new data about an intervention or medical condition metric.

11. The method of claim 9, further comprising:
    displaying the new data along with the post on the interactive environment.

12. The method of claim 1, wherein the relevant data is displayed in a graphical element.

13. The method of claim 11, wherein the graphical element is a chart.

14. The method of claim 1, further comprising:
    receiving a response from a second pre-identified user;

automatically identifying and selecting relevant data about the second pre-identified user from a database, the relevant data about the second pre-identified user selected based on information contained in the response received from the second pre-identified user; and displaying the relevant data about the second pre-identified user to other users along with the response on the interactive environment.

15. A non-transitory and tangible computer-readable medium whose contents cause a computer to perform a method for context-linked identification and importation of user information from a database into an interactive environment implemented on a computer and accessible to other users, the method comprising:

providing the interactive environment on the computer that allows posting of content by a plurality of pre-identified users;

receiving first content on the computer for the interactive environment from a first pre-identified user;

automatically identifying and selecting on the computer relevant data about the first pre-identified user from a database based on the first content posted by the first pre-identified user, the relevant data selected from data previously-submitted by the first pre-identified user based on information contained in the first content posted by the first pre-identified user by:

identifying one or more relevant terms for the first content by (i) performing natural language processing on the first content, (ii) parsing one or more tags applied to the first content, or (iii) forming an inference based on the first content; and selecting relevant data from the database based on the one or more relevant terms; and displaying via the computer the relevant data to other users along with the first content on the interactive environment.

16. A system for the context-linked identification and importation of user information from a database into an interactive environment implemented on a computer and accessible to other users, the system comprising:

a database; and a server in communication with the database, the server configured to:

provide an interactive environment that allows posting of content by a plurality of pre-identified users;

receive first content for the interactive environment from a first, pre-identified user;

automatically identify and select relevant data about the first, pre-identified user from a database based on the first content posted by the first pre-identified user, the relevant data selected from data previously-submitted by the first pre-identified user based on information contained in the first content posted by the first pre-identified user by:

identifying one or more relevant terms for the first content by (i) performing natural language processing on the first content, (ii) parsing one or more tags applied to the first content, or (iii) forming an inference based on the first content; and selecting relevant data from the database based on the one or more relevant terms; and display the relevant data to other users along with the first content on the interactive environment.

17. The method of claim 1, wherein said network is the Internet.

18. A method for context-linked identification and importation of user information from a database containing user information into an interactive forum hosted on a computer and accessible to other users via a network, the method comprising:

receiving data on the computer from a first pre-identified user regarding the pre-identified user's medical status or medical history;

storing the data on the computer about the first pre-identified user's medical status or medical history in a database;

providing an interactive forum on the computer that allows posting and display of content related to medical topics by a plurality of pre-identified users;

receiving first content on the computer related to medical topics for the interactive environment from a first pre-identified user;

automatically identifying and selecting on the computer relevant data about the first pre-identified user's medical status or medical history from the database based on the first content posted by the first pre-identified user, the relevant data selected based on information contained in the first content posted by the first pre-identified user by:

identifying one or more relevant terms for the first content by (i) performing natural language processing on the first content, (ii) parsing one or more tags applied to the first content, or (iii) forming an inference based on the first content; and selecting relevant data from the database based on the one or more relevant terms; and displaying via the computer the relevant data about the first pre-identified user's medical status or medical history to other users along with the first content on the interactive forum.

19. The method of claim 1, wherein the relevant data includes data submitted by the first pre-identified user after posting of the first content by the pre-identified user in the interactive forum.

* * * * *